United States Patent [19]

Quigley, Jr. et al.

[11] 4,335,471
[45] Jun. 22, 1982

[54] HEADGEAR

[76] Inventors: Richard I. Quigley, Jr.; Penny P. Quigley, both of 1800 Windsor Dr., High Point, N.C. 27260

[21] Appl. No.: 206,460

[22] Filed: Nov. 13, 1980

[51] Int. Cl.³ .......................... A42B 1/20; A61F 9/00
[52] U.S. Cl. ............................................. 2/12; 2/200
[58] Field of Search ................... 2/12, 175, 177, 195, 2/209.1, 200; 40/586

[56] References Cited

U.S. PATENT DOCUMENTS

| 2,081,088 | 5/1937 | Guntrup | 2/12 |
| 2,769,308 | 11/1956 | Krasno | 2/200 UX |
| 4,096,589 | 6/1978 | Goldstein | 2/12 |
| 4,246,659 | 1/1981 | Lyons | 2/175 |

FOREIGN PATENT DOCUMENTS

| 96878 | 9/1939 | Sweden | 2/12 |
| 416163 | 9/1934 | United Kingdom | 2/12 |

Primary Examiner—Peter P. Nerbun

[57] ABSTRACT

Headgear is formed of resilient material such as foam rubber and includes a display panel joined to a head encircling portion or band. When not worn the display panel remains in a flat, horizontal posture and when placed on the wearer's head the display panel pivots to assume an erect posture.

5 Claims, 7 Drawing Figures

HEADGEAR

BACKGROUND AND OBJECTIVES OF INVENTION

At sporting events such as football or basketball games fans are often desirous of wearing hats, caps or other headgear to demonstrate to others the team they are rooting for. School colors, emblems, slogans and other displays are often attached to various headgear to demonstrate a fan's loyalty. Hat bands are often used to retain slogan cards, advertisements, and other paraphernalia for particular wearers. With this background in mind the present invention was conceived and one of its purposes is to provide light-weight headgear which includes a display panel on which a slogan or emblem can be printed directly thereon or for attachment of such materials.

It is another objective of the present invention to provide headgear composed of polyurethane foam rubber or other resilent material which will readily conform to a wearer's head.

It is yet another objective of the present invention to provide headgear which will fit a variety of head sizes.

It is still another objective of the present invention to provide headgear which is light in weight and inexpensive to manufacture and easy to store in a compact fashion.

It is still another objective of the present invention to provide headgear which includes an integral display panel and visor portion.

SUMMARY OF THE PREFERRED EMBODIMENT OF THE INVENTION

The preferred embodiment of the invention contained herein consists of headgear formed from a resilent material such as polyurethane foam rubber which includes in the relaxed or unworn state a flat or prostrate display panel. A head encircling portion or band is joined to the panel member and when the headgear is worn the stress which results from stretching of the head encircling band causes the display panel member to assume a raised or erect position. The visor portion of the headgear which is attached to the outer edge of the headband pivots with the panel member when the headgear is worn and assumes a descending posture. When the headgear is removed from the wearer the stress in the band is relieved and the panel member and visor return to a recumbent attitude for easy, compact storage in a drawer or other convenient location.

DESCRIPTION OF THE DRAWINGS

Turning now to the drawings.

Figure 1:
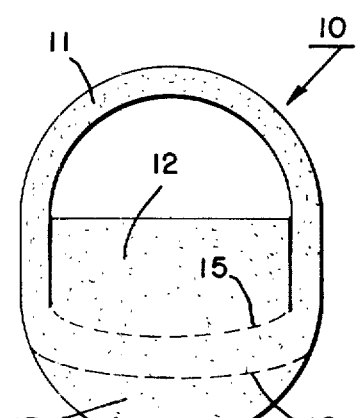
FIG. 1 demonstrates a top view of the headgear of the present invention in an unworn, relaxed state.

For a more detailed description of the drawings, FIG. 1 demonstrates the preferred embodiment of headgear 10 in a relaxed condition. (Relaxed herein refers to the headgear not being worn). Headgear 10 includes the head encircling band or portion 11, a display panel 12, and a visor portion 13. Headgear 10 can be constructed for example by die cutting flat polyurethane sheets having a density of 1.25 pounds per cubic foot although other densities may also be used. A desirable thickness has been found to be one half inches for the uncut polyurethane foam sheets although other thicknesses may be selected if desired.

Figures 4, 7:
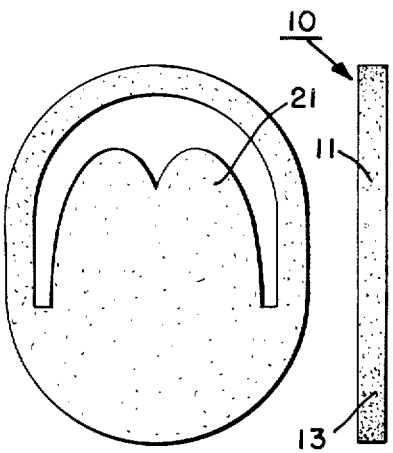
FIG. 4 demonstrates a different configuration of the display panel from that shown in FIGS. 1 and 3.
FIG. 7 demonstrates a side view of the headgear when not being worn with the panel member (not shown) being in a recumbent position.
Figure 6:
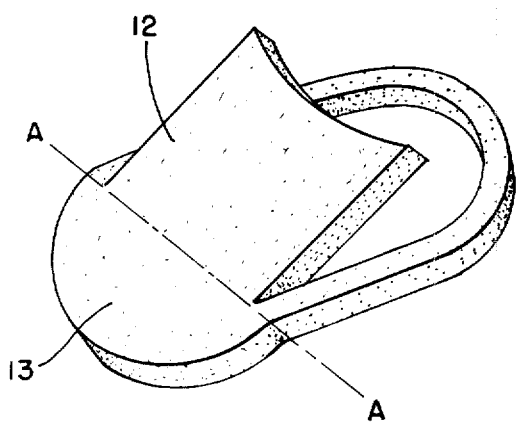
FIG. 6 demonstrates the display panel in somewhat of an erect posture as would occur when the headgear is worn.
Figure 2:
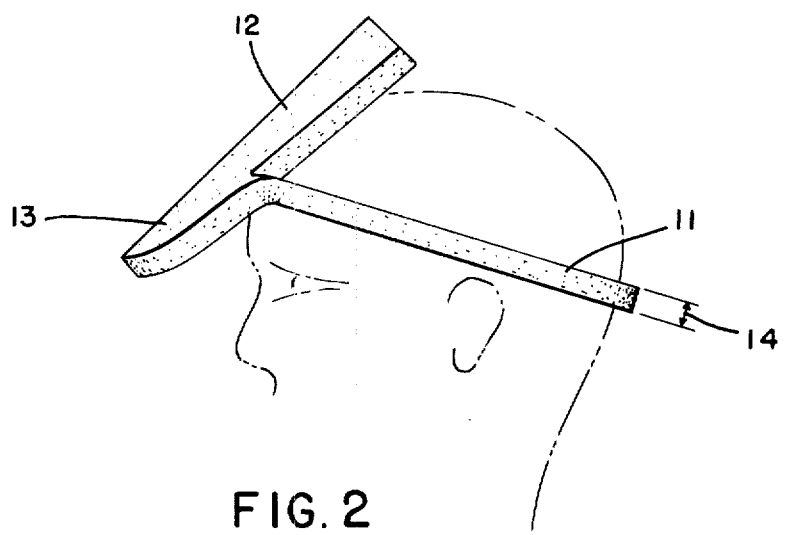
FIG. 2 demonstrates the headgear as shown in FIG. 1 being worn with the display panel erect.

As shown in FIG. 2 the thickness of encircling band 11 illustrated by arrow 14 is somewhat reduced from the thickness shown in FIG. 7 since encircling band 11 is in a stretched or drawn state conforming to the shape of the wearer's head. Also in FIG. 2 display panel 12 is shown in its raised posture with visor portion 13 assuming a descending attitude. Visor portion 13 pivots with display panel 12 approximately along line A—A as shown in FIG. 6.

The dotted line 15 as shown in FIG. 1 illustrates the approximate inside dimension of head encircling portion 11 where the display panel begins and dotted line 16 approximates the rear portion of the visor member 13.

Figure 3:
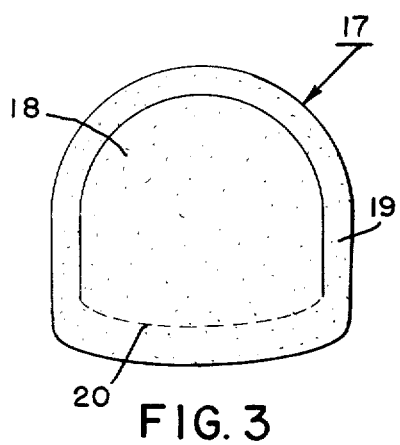
FIG. 3 demonstrates an embodiment of the headgear without a visor portion.

In another embodiment, head gear 17 is shown in FIG. 3 having a large display panel 18 which is attached to encircling band 19 along dotted line 20 and this particular embodiment has no visor portion.

Figure 5:
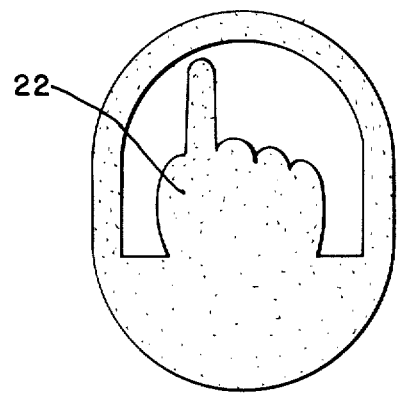
FIG. 5 demonstrates still another embodiment of the display panel of the headgear.

In FIG. 4 an "M" display panel 21 is shown and in FIG. 5 display panel 22 illustrates a closed fist with the index finger extended to demonstrate the popular symbol of "No. 1".

The side view of headgear 10 is shown in FIG. 7 and as it is understood that inside encircling band 11, display panel 12 remains in a prostrate position, which is not shown in FIG. 7.

While polyurethane foam of suitable density has been used other materials including various types of foam such as nylon may also be used in part or entirely to construct the present invention although it has been found that resilient polyurethane conforms to the wearer's head readily and is comfortable during extended periods of wear such as through the course of a ball game. Also, headgear as contained herein may have its display panel or visor composed of other materials and may be formed by joining various components as opposed to an integral construction as shown in FIG. 1.

Other modifications and changes may be advisable under desired conditions and the examples as shown herein are not intended to limit the scope of the invention.

I claim:

1. Headgear comprising: a resilient head encircling portion, a part of said encircling portion extending behind the wearer's head in a continuous manner from one side of the head to the other, said encircling portion contourable at least in part to the shape of the wearer's head, a display panel, said panel affixed to said encircling band, a visor portion, said visor portion integrally formed with said panel and pivotable therewith and said display panel pivotable from a prostrate to a raised position.

2. Headgear as claimed in claim 1 wherein said resilent portion comprises polyurethane foam rubber.

3. Headgear as claimed in claim 1 wherein said display panel is affixed to the inside of said encircling band.

4. Headgear comprising: a resilent head encircling portion contourable to the shape of the wearer's head, a part of said encircling portion extending behind the wearer's head in a continuous manner from one side of the head to the other, a pivotable display panel joined to said encircling portion, said display panel having a prostrate posture when the headgear is in a relaxed position, and having a raised posture when the headgear is worn, a visor portion, said visor portion integrally formed and pivotable with said display panel whereby said visor portion assumes a descending attitude when said display panel is in a raised posture.

5. Headgear as claimed in claim 4 composed of polyurethane foam rubber.

* * * * *